United States Patent
Leinen et al.

(10) Patent No.: US 6,682,719 B2
(45) Date of Patent: *Jan. 27, 2004

(54) PLAQUE-CONTROLLING LIQUID TOOTH CLEANING AGENT

(75) Inventors: Hans-Theo Leinen, Duesseldorf (DE); Dorothea Gregori, Neuss (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/268,462

(22) Filed: Oct. 10, 2002

(65) Prior Publication Data

US 2003/0108491 A1 Jun. 12, 2003

Related U.S. Application Data

(63) Continuation of application No. PCT/EP01/03698, filed on Mar. 31, 2001.

(30) Foreign Application Priority Data

Apr. 11, 2000 (DE) .......................... 100 17 997

(51) Int. Cl.$^7$ ................................. A61K 7/16
(52) U.S. Cl. .......................................... 424/49
(58) Field of Search ..................... 424/49–88

(56) References Cited

U.S. PATENT DOCUMENTS

| | | | |
|---|---|---|---|
| 3,538,230 A | | 11/1970 | Pader et al. |
| 3,689,637 A | | 9/1972 | Pader |
| 4,067,746 A | | 1/1978 | Wason et al. |
| 4,108,978 A | * | 8/1978 | Mazzanobile et al. ........ 424/49 |
| 4,153,680 A | | 5/1979 | Seybert |
| 4,435,380 A | * | 3/1984 | Pader ........................... 424/49 |
| 4,857,289 A | | 8/1989 | Nauroth et al. |
| 4,891,211 A | * | 1/1990 | Winston ........................ 424/49 |
| 4,943,429 A | * | 7/1990 | Winston et al. ................ 424/49 |
| 5,178,869 A | * | 1/1993 | Ebine et al. .................... 424/49 |
| 5,456,745 A | * | 10/1995 | Roreger et al. ............. 106/128 |
| 5,622,168 A | * | 4/1997 | Keusch et al. ............... 252/500 |
| 5,628,985 A | * | 5/1997 | Stiller et al. ................... 424/49 |
| 5,858,333 A | * | 1/1999 | Winston et al. ................ 424/49 |
| 6,342,205 B1 | * | 1/2002 | Niemi et al. ................... 424/49 |
| 6,506,366 B1 | * | 1/2003 | Leinen et al. .................. 424/49 |

FOREIGN PATENT DOCUMENTS

| | | |
|---|---|---|
| CA | 2 140 370 | 1/1994 |
| CA | 2 006 707 | 1/2001 |
| DE | 20 33 678 | 5/1971 |
| DE | 25 22 486 A1 | 11/1975 |
| DE | 31 14 493 A1 | 10/1982 |
| DE | 198 45 247 A1 | 4/2000 |
| EP | 0 549 287 A1 | 6/1993 |
| EP | 0 754 027 B1 | 10/1999 |
| FR | 2 684 550 A1 | 6/1993 |
| GB | 2 227 661 A | 8/1990 |
| WO | WO 94/01080 A2 | 1/1994 |
| WO | WO 94/23691 A2 | 10/1994 |

* cited by examiner

*Primary Examiner*—Shep K. Rose
(74) *Attorney, Agent, or Firm*—Stephen D. Harper; Gregory M. Hill

(57) ABSTRACT

There is provided a water-based liquid tooth cleaning gel with a viscosity below 50 Pa·s (20° C.), comprising

| | |
|---|---|
| 10 to 20% by weight of | silica polishes, |
| 40 to 60% by weight of | a humectant composition consisting of less than 50% by weight of sorbitol, less than 10% by weight of glycerol and 0.1% to 5% by weight of polyethylene glycol with an average molecular weight of 800 to 10,000, |
| 0.1 to 1% by weight of | an antimicrobial agent selected from the group consisting of triclosan, hexetidine and mixtures thereof, |
| 1 to 10% by weight of | other toothpaste ingredients and |
| 25–35% by weight of | water. |

6 Claims, No Drawings

PLAQUE-CONTROLLING LIQUID TOOTH CLEANING AGENT

CROSS REFERENCE TO RELATED APPLICATIONS

This application is a continuation under 35 U.S.C. §365 (c) and §120 of International Application No. PCT/EP01/03698 filed Mar. 31, 2001 and under §119 of German Patent Application No. 100 17 997.5 filed Apr. 11, 2000.

SUMMARY OF THE INVENTION

This invention relates to liquid tooth cleaning preparations containing polishes, humectants, tartar-inhibiting antimicrobial agents and water which are substantially transparent or clear and which show favorable rheological behavior for dispensing from small flexible plastic bottles.

BACKGROUND OF THE INVENTION

Liquid tooth cleaning preparations which can be dispensed under light pressure from small flexible plastic bottles are already known, for example from WO 94/01080 A1. These products are white or opaque in appearance. DE 2033678 B2 describes toothpastes which contain a silica polish and a humectant combination containing polyethylene glycols with molecular weights in the range from 800 to 2,000. These products are clear or transparent in appearance. EP 0 754 027 B2 describes liquid tooth cleaning preparations containing a silica polish and a humectant combination of sorbitol and a low molecular weight polyethylene glycol.

The problem addressed by the present invention was to provide water-based liquid tooth cleaning gels having high transparency and a content of antimicrobial agents for controlling tartar. It has been found that both the liquid consistency and high transparency can be achieved if the products contain less than 50% by weight of sorbitol and 0.1 to 5% by weight of a polyethylene glycol with an average molecular weight of 800 to 10,000 and 0.1 to 1% by weight of an antimicrobial agent selected from triclosan, hexetidine and mixtures thereof.

DESCRIPTION OF THE INVENTION

Accordingly, the present invention relates to a water-based liquid tooth cleaning gel with a viscosity below 50 Pa·s (20° C.), characterized by a content of

| | |
|---|---|
| 10 to 20% by weight of | a silica polish, |
| 40 to 60% by weight of | a humectant combination consisting of less than 50% by weight of sorbitol (based on the gel as a whole), less than 10% by weight of glycerol and 1 to 5% by weight of polyethylene glycol with an average molecular weight of 800 to 10,000, |
| 0.1 to 1% by weight of | an antimicrobial agent selected from triclosan, hexetidine and mixtures thereof, |
| 1 to 10% by weight of | other toothpaste ingredients and |
| 25 to 35% by weight of | water. |

Liquid in the context of the present invention means a viscosity of less than 50 Pa·s (as measured at 20° C. with a Brookfield RVF rotational viscosimeter, spindle ¾ at 4 r.p.m. corresponding to a shear rate D of 4 $S^{-1}$) which provides for dispensing from a small flexible bottle by light pressure and ensures that the gel sinks slowly into the bristles of the toothbrush.

The transparency of the tooth cleaning gel should be at least so high that text with a letter height of ca. 4 mm and a letter width of 3 mm is still easy to read through a ca. 1 cm thick layer of the tooth gel (for example in a clear glass cell with an edge length of 1×1×4 cm). The viscosity and transparency according to the invention are achieved through the choice and quantity of the polishing components, thickeners and humectants used.

Suitable silica polishing components are any silica gels, silica hydrogels and precipitated silicas known as polishes. Silica gels are obtained by reacting sodium silicate solutions with strong aqueous mineral acids to form a hydrosol, ageing to form the hydrogel, washing and drying. If drying is carried out under moderate conditions to a water content of 15 to 35% by weight, the so-called silica hydrogels known, for example, from U.S. Pat. No. 4,153,680 are obtained.

Drying to water contents below 15% by weight results in irreversible shrinkage of the previously loose structure of the hydrogel to the dense structure of the so-called xerogel. Silica xerogels are described, for example, in U.S. Pat. No. 3,538,230.

A second particularly suitable group of silica polishing agents are the precipitated silicas. Precipitated silicas are obtained by precipitation of silica from dilute alkali metal silicate solutions by addition of strong acids under conditions which preclude aggregation to the sol and gel. Suitable processes for the production of precipitated silicas are described, for example, in DE-OS 25 22 486 and in DE-OS 31 14 493. A particularly suitable precipitated silica is that produced in accordance with DE-OS 31 14 493 which has a BET surface of 15 to 110 $m^2/g$, a particle size of 0.5 to 20 μm (at least 80% by weight of the primary particles should be below 5 μm in size) and a viscosity in the form of a 30% glycerol/water (1:1) dispersion of 30 to 60 Pa·s (20° C.) and which is used in a quantity of 10 to 20% by weight, based on the tooth gel. In addition, particularly suitable precipitated silicas of this type have rounded corners and edges and are commercially obtainable under the name of Sident®12 DS (DEGUSSA). Another suitable silica is Zeodent 113 (Huber Corp.) with a BET surface of 150 to 250 $m^2/g$.

Other precipitated silicas of this type are Sident 8 (DEGUSSA) and Sorbosil AC 39 (Crosfield Chemicals). These silicas are distinguished by a weaker thickening effect and a slightly larger mean particle size of 8 to 14 μm for a specific BET surface of 40 to 75 $m^2/g$ and are particularly suitable for liquid tooth gels according to the present invention.

Other polishes, particularly those with a refractive index differing from 1.45 μm by more than 0.1, are preferably not present at all or are present at most in quantities of less than 2% by weight. Such polishes are, for example, pumice, zirconium silicate or gamma-aluminium oxide.

Of crucial importance to the rheology and transparency of the liquid tooth cleaning gels according to the invention is the composition of the liquid carrier phase of water and humectants. The total quantity of 40 to 60% by weight of the humectant combination is based on the tooth cleaning gel as a whole and consists essentially of sorbitol and polyethylene glycol. However, the quantity of sorbitol should be below 50% by weight. Glycerol may optionally be present in quantities of less than 10% by weight. Suitable polyethylene glycols are the relatively high molecular weight types with average molecular weights of 800 to 10,000 and preferably in the range from 1,000 to 40,000. The water content of the tooth gels according to the invention is in the range from 25 to 35% by weight and is the sum of the quantities of water introduced by the raw materials, such as 70% sorbitol or 86% glycerol for example, and the quantities separately added. The quantities of sorbitol and glycerol mentioned are based on water-free active substances.

Particularly suitable antimicrobial agents for inhibiting the formation of plaque are 2,2,4'-trichloro-2'-hydroxydiphenylether (triclosan) and 1,3-bis-(2-ethylhexyl)-5-mthyl-5-aminohexahydropyrimidine (hexetidine) and mixtures of these antimicrobial components. The hexetidine may also be present in the form of a water-soluble salt, for example the benzoate, terephthalate or salicylate. These selected antimicrobial agents can be incorporated particularly clearly and stably in the tooth gels according to the invention.

In addition to the compulsory components mentioned, the tooth cleaning gels according to the invention may contain 1 to 10% by weight of other toothpaste ingredients which, in type and quantity, do not adversely affect transparency. Such ingredients are, for example, binders, surfactants, flavors and sweeteners, scale inhibitors, fluorine compounds, vitamins, panthenol and other active substances.

Suitable binders are, for example, natural and/or synthetic water-soluble polymers, such as alginates, carrageenates, tragacanth, starch and starch ethers, cellulose ethers such as, for example, carboxymethyl cellulose (Na salt), hydroxyethyl cellulose, methyl hydroxypropyl cellulose, guar, acacia gum, agar agar, xanthan gum, succinoglycan gum, locust bean gum, pectins, water-soluble carboxyvinyl polymers (for example Carbopol® types), polyvinyl alcohol, polyvinyl pyrrolidone, polyethylene glycols, more particularly those with molecular weights of 1,500 to 1,000,000.

Particularly suitable binders are xanthan gum, carboxymethyl cellulose, polyvinyl pyrrolidone and mixtures of these water-soluble polymers which may be present in a quantity of up to 1.0% by weight.

Suitable surfactants are, for example, sodium alkyl sulfates containing 12 to 18 carbon atoms in the alkyl group. These compounds also have an enzyme-inhibiting effect on the bacterial metabolism of tartar. Other suitable surfactants are alkali metal salts, preferably sodium salts of alkyl polyglycol ether sulfate containing 12 to 16 carbon atoms in the linear alkyl group and 2 to 6 glycol ether groups in the molecule, of linear alkane ($C_{12-18}$) sulfonate, of sulfosuccinic acid monoalkyl ($C_{12-18}$) esters, of sulfated fatty acid monoglycerides, sulfated fatty acid alkanolamides, sulfoacetic acid alkyl ($C_{12-16}$) esters, acyl sarcosines, acyl taurides and acyl isethionates containing 8 to 18 carbon atoms in the acyl group.

Ampholytic and zwitterionic surfactants, more particularly betaine surfactants, for example cocoalkyl betaine or cocoacylamidopropyl betaine, are also suitable. Finally, nonionic surfactants, for example ethoxylates of fatty acid mono- and diglycerides, of fatty acid sorbitan esters and alkyl (oligo)glucosides, may also be used.

In a preferred embodiment, the tooth cleaning gels according to the invention contain a water-soluble binder and a surfactant combination of anionic, zwitterionic and nonionic surfactants as further ingredients. The surfactants are preferably present in a quantity of 0.5 to 3% by weight, the quantity ratio of anionic to zwitterionic and nonionic surfactants preferably being 1:(0.2–1).

Flavors and sweeteners are normally used for flavoring. Suitable flavors are, for example, peppermint oil, spearmint oil, eucalyptus oil, aniseed oil, fennel oil, caraway oil, methyl acetate, cinnamaldehyde, anethol, vanillin, thymol and other natural or nature-identical essential oils or even synthetic flavors.

Suitable sweeteners are, for example, saccharin sodium, acesulfam, aspartame, sodium cyclamate, steviosides, thaumatine, sucrose, lactose, maltose or fructose, glycyrrhizin, etc.

Suitable scale inhibitors are, for example, organic phosphonates, such as azacycloheptane-2,2-diphosphonic acid disodium salt or 1-hydroxyethane-1,1-diphosphonic acid tetrasodium salt. Suitable fluorine compounds are, for example, sodium fluoride and sodium monofluorophosphate ($Na_2PO_3F$).

The vitamins present may be selected, for example, from retinol, panthenol or a salt of pantothenic acid, ascorbic acid or mixtures thereof. In a preferred embodiment, a combination of panthenol and retinol is present for improving the inflammation-inhibiting properties.

In addition, a content of certain dissolved divalent metal salts, more particularly salts of magnesium and zinc, has proved to be valuable for the remineralizing properties of the tooth cleaning gels according to the invention. Suitable metal salts are, for example, the sulfates, fluorides, citrates or acetates of these metals. A preferred embodiment is characterized by the presence of dissolved salts of magnesium or zinc or a mixture of both salts in a quantity of 0.02 to 0.2% by weight $Mg^{++}$ and/or $Zn^{++}$.

The tooth cleaning gels according to the invention may additionally contain, for example, buffering agents, for example primary, secondary or tertiary alkali metal phosphates, citric acid/Na citrate, wound-healing and anti-inflammatory agents such as, for example, urea, allantoin, camomile-based active principles, such as azulene, alkali metal thiocyanate, acetylsalicylic acid derivatives, lower alcohols, for example ethanol, isopropanol, and dyes and pigments.

The following Examples are intended to illustrate the invention.

EXAMPLES

Liquid tooth cleaning gels with the following composition were produced:

|  | 1 | 1 | 3 | 4 | 5 | C1 | C2 |
|---|---|---|---|---|---|---|---|
| Sident 8 | 12 | 12 | 12 | — | — | 12 | 12 |
| Zeodent 113 | — | — | — | — | 12 | — | — |
| RP-LA-2981 | — | — | — | 12 | — | — | — |
| Sorbitol | 49 | 49 | 49 | 49 | 49 | 49 | 49 |
| Lipoxol 1550 | 1.5 | 1.5 | 1.5 | 1.5 | 1.5 | — | — |
| Lipoxol 400 | — | — | — | — | — | 2.0 | 2.0 |
| Cekol 200 | 0.5 | 0.5 | 0.5 | 0.5 | 0.5 | 0.5 | 0.5 |
| Tagat S | 0.5 | 0.5 | 0.5 | 0.5 | 0.5 | 0.5 | 0.5 |
| Tego Betain BL 215 | 0.6 | 0.6 | 0.6 | 0.6 | 0.6 | 0.6 | 0.6 |
| Texapon K1296 | 1.5 | 1.5 | 1.5 | 1.5 | 1.5 | 1.5 | 1.5 |
| $MgSO_4 \cdot 7H_2O$ | — | 0.5 | 0.5 | — | — | — | 0.5 |
| $ZnSO_4 \cdot 7H_2O$ | — | 0.16 | — | 0.16 | 0.16 | — | 0.16 |
| $Na_2PO_3F$ | 1.1 | 1.1 | 1.1 | 1.1 | 1.1 | 1.1 | 1.1 |
| $Na_2HPO_4$ | 0.2 | 0.2 | 0.2 | 0.2 | 0.2 | 0.2 | 0.2 |
| Na saccharinate | 0.2 | 0.2 | 0.2 | 0.2 | 0.2 | 0.2 | 0.2 |
| Flavoring oil | 1.0 | 1.0 | 1.0 | 1.0 | 1.0 | 1.0 | 1.0 |
| Triclosan | 0.1 | 0.1 | 0.1 | 0.1 | 0.1 | 0.1 | 0.1 |
| Ethanol | 2.0 | 2.0 | 2.0 | 2.0 | 2.0 | 2.0 | 2.0 |
| Water | to 100 | to 100 | to 100 | to 100 | to 100 | to 100 | to 100 |
| Transparency | 1 | 1 | 2 | 2 | 2 | 3 | 4 |

Transparency was visually evaluated as follows:
1: clear to highly transparent
2: transparent
3: slightly transparent to slightly cloudy
4: opaque The following commercial products were used:

Sident 8 (Degussa-Hüls):
  Hydrogel silica, BET surface 60 $m^2/g$
Zeodent 113 (Huber Corp.):
  Hydrogel silica, BET surface 150–250 $m^2/g$
Silica RP-LA-2981 (Rhone Poulenc):
  Precipitated silica
Cekol 2000 (Metsa):
  Sodium carboxymethyl cellulose, viscosity (2%, 25 C): 1.3–2.3 Pa·s
Tagat S (Goldschmidt):
  PEG 30 Glyceryl Stearate
Tego Betain BL 215 (Goldschmidt):
  Fatty acid amidoalkyl betaine (30%), Cocoamidopropyl Betaine
Texapon K 1296 (Cognis Deutschland):
  Sodium lauryl sulfate (powder), anionic surfactant content min. 94% by wt.
Lipoxol 1550 (RWE/DEA):
  Polyethylene glycol, molecular weight 1550
Lipoxol 400 (RWE/DEA):
  Polyethylene glycol, molecular weight 400

What is claimed is:

1. A water-based liquid tooth cleaning gel with a viscosity below 50 Pa·s (20° C.), comprising

| 10 to 20% by weight of | silica polishes, |
|---|---|
| 40 to 60% by weight of | a humectant composition consisting of less than 50% by weight of sorbitol, less than 10% by weight of glycerol and 0.1 to 5% by weight of polyethylene glycol with an average molecular weight of 800 to 10,000, |
| 0.1 to 1% by weight of | an antimicrobial agent selected from the group consisting of triclosan, hexetidine and mixtures thereof, |
| 1 to 10% by weight of | other toothpaste ingredients and |
| 25 to 35% by weight of | water. |

2. The liquid tooth cleaning gel of claim 1, wherein a water-soluble binder and a surfactant combination of anionic, zwitterionic and nonionic surfactants are present as further ingredients.

3. The liquid tooth cleaning gel of claim 2, wherein a dissolved salt of magnesium or zinc or a mixture of both salts is present as a further ingredient in a quantity of 0.02 to 0.2% by weight $Mg^{++}$ and/or $Zn^{++}$.

4. The liquid tooth cleaning gel of claim 1 wherein the silica polishes are selected from the group consisting of silica gels, silica hydrogels and precipitated silicas.

5. The liquid tooth cleaning gel of claim 2 wherein the surfactant composition is present in a quantity of from 0.5 to 3% by weight and where the quantity ratio of anionic to zwitterionic and nonionic surfactants is 1:(0.2–1).

6. The liquid tooth cleaning gel of claim 1, wherein a dissolved salt of magnesium or zinc or a mixture of both salts is present as a further ingredient in a quantity of 0.02 to 0.2% by weight $Mg^{++}$ and/or $Zn^{++}$.

* * * * *